United States Patent [19]

Kurscheidt et al.

[11] Patent Number: 5,343,868
[45] Date of Patent: Sep. 6, 1994

[54] METHOD AND APPARATUS FOR DETECTING ARTIFACTS IN A BLOOD PRESSURE MEASURING SYSTEM

[75] Inventors: Regina Kurscheidt, Solingen; Martin Felger, Tuebingen, both of Fed. Rep. of Germany; Michael P. Beech, Bristol, United Kingdom

[73] Assignee: Hewlett-Packard Company, Palo Alto, Calif.

[21] Appl. No.: 38,672

[22] Filed: Mar. 26, 1993

[30] Foreign Application Priority Data

Apr. 2, 1992 [EP] European Pat. Off. ........ 92105665.1

[51] Int. Cl.⁵ .......................................... A61B 5/0215
[52] U.S. Cl. ..................................... 128/673; 128/672
[58] Field of Search ............................. 128/672–673, 128/677, 680–683, 748

[56] References Cited

U.S. PATENT DOCUMENTS 4,223,681 9/1980 Sherman ........................ 128/672
4,223,682 9/1980 Sherman ........................ 128/672
4,667,680 5/1987 Ellis .
4,777,959 10/1988 Wallach et al. ................. 128/677
5,014,714 5/1991 Millay et al. .................... 128/672

FOREIGN PATENT DOCUMENTS

WO9100113 1/1991 World Int. Prop. O. .

OTHER PUBLICATIONS

Biomedizinische Technik, vol. 33, No. 9, Sep. 1988, Berlin, DE pp. 210–214.

*Primary Examiner*—Angela D. Sykes

[57] ABSTRACT

A method for detecting artifacts in a blood pressure measuring system, in particular artifacts caused by sampling or flushing in an invasive blood pressure measuring system, disables the related alarms if a sample in a time sequence is larger than a mean value, and when it exceeds a predetermined limit, and when its slope is beyond another limit, and if all of these conditions apply for a certain time period. The end of an artifact is detected if the slope falls beyond a limit, a pulsation is detected, the absolute value is beyond a limit for a certain amount of time, or a long timeout occurs.

19 Claims, 9 Drawing Sheets

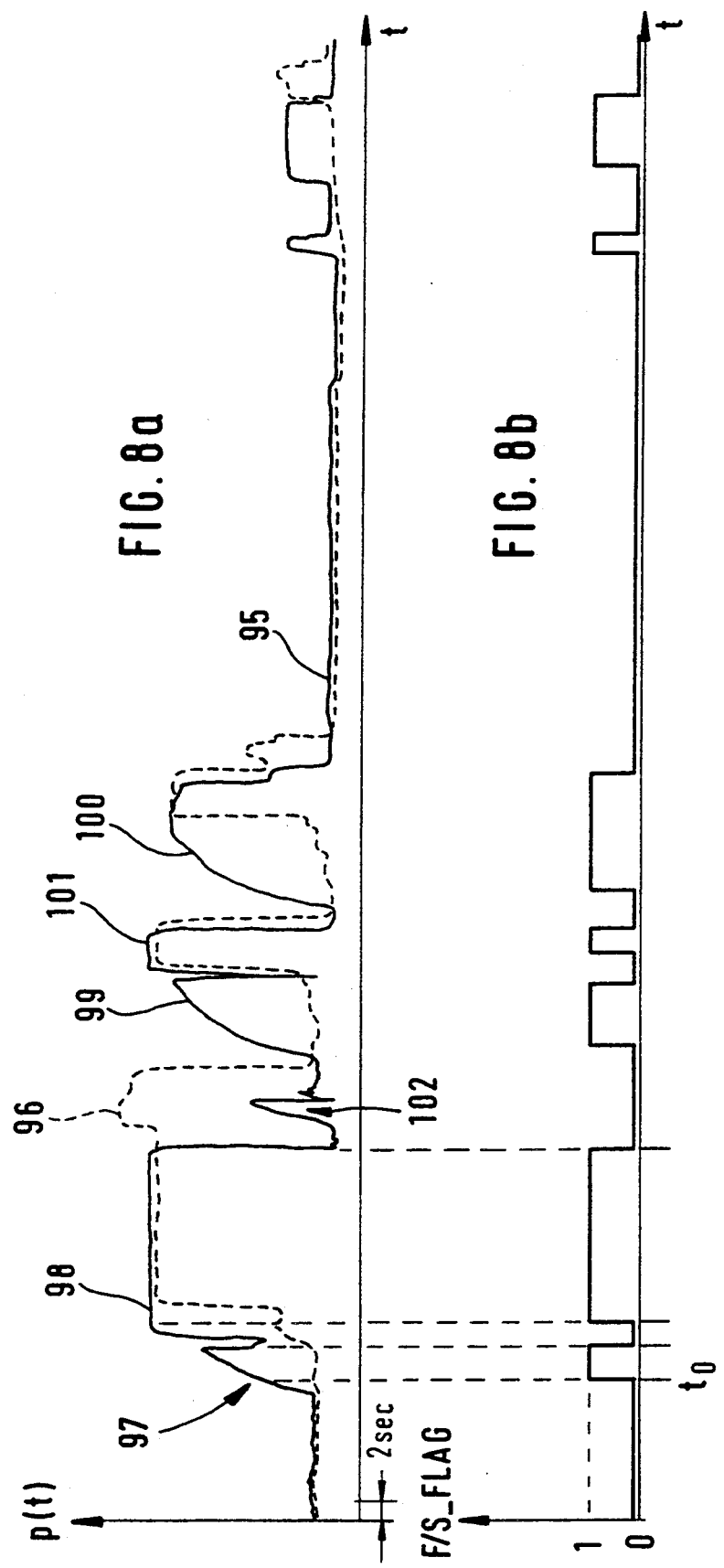

METHOD AND APPARATUS FOR DETECTING ARTIFACTS IN A BLOOD PRESSURE MEASURING SYSTEM

FIELD OF THE INVENTION

The present invention relates to the field of medical monitoring, in particular blood pressure monitoring. More specifically, it deals with a method for detecting artificial artifacts in a blood pressure measuring system.

DESCRIPTION OF THE PRIOR ART

It is a primary purpose of medical monitors not only to display or record vital signs such as the electrocardiogram, respiration, the blood pressure etc. of a patient (whether in graphical or numerical form), but also to attract the attention of medical personnel in case a physiological parameter shows a suspicious or pathologic pattern. Usual techniques to alarm or alert the nurse or the doctor comprise acoustic or visual alarming means (such as flashing and/or colored numerics on the screen of a monitor, or a beeper) which are activated in case a physiological parameter exceeds a predefined (and/or adjustable) limit; e.g., an alarm is generated if the heart rate or the blood pressure exceed an upper limit, or fall below a lower limit.

Such alarms are essential for patient care and patient safety. Therefore, the alarming system is usually quite sensitive to the occurrence of alarming conditions.

However, highly sensitive alarm monitoring implies that the alarm system occasionally triggers on conditions which do not really indicate a serious risk to the patient. Such alarms are called false-positive alarms. They do unnecessarily distract medical personnel from more important tasks, and the occurrence of a significant number of false-positive alarms may also impact the confidence in the monitor's alarming capabilities. Even worse, the habituation to frequent false-positive alarms may be the reason that real alarms (i.e. alarms which effectively indicate a dangerous situation of the patient and require immediate action) are ignored, or otherwise escape the attention of medical personnel. Needless to say that this habituation effect implies serious risks for the patient.

It is thus a primary design goal of medical monitoring devices to keep the number of false-positive alarms as low as possible.

It is evident that any measures which decrease the sensitivity of the alarming system (e.g., a reduction of the number of performed tests, or making the alarming limits less sensitive) are not a suitable solution of the underlying problem, as such measures may also suppress real alarms. However, there are frequently situations where a false-positive alarm is caused by events which are unrelated to the monitored parameter. Such events may originate from the patient itself—e.g., patient movement—, from external measures, such as surgery with a radio knife (electrosurgery), or they may originate from other sources (e.g., environmental noise). Some of these events produce characteristic patterns which are detectable by electronic equipment; for example, electrosurgery produces noise in a frequency range which is different from the useful spectral components in an electrocardiogram, such that the useful signal and the noise can be separated by a filter with appropriate band limits.

Techniques to suppress components which are unrelated to a physiological signal (and thus are useful to avoid false-positive alarms) are known as "artifact suppression". The above considerations show that such techniques may particularly be provided if the disturbing signal (the artifact) contains components that are at least partially different from the components of the useful signal. (Such differing components may be spectral components, as well as characteristics in the time domain.) It will be appreciated that these differences occur especially in noise (hereinafter called "artificial artifacts") originating from external sources which generate a disturbing signal with basically known components in the time domain and/or frequency domain.

Despite the undeniable advantages of artifact suppression, in practice only little use has been made of it. This is mainly due to the technical problems encountered with artifact detection. In the vast majority of cases, the time/frequency characteristics of the artifact are not precisely known, or they are not repeatable (i.e., they differ significantly from case to case), or they overlap partially (or at least in some cases) with the useful physiological signal. In the latter case, artifact detection/suppression cannot be provided at all, because there is the risk of suppressing "real" physiological alarms, such that an emergency situation will not be recognized.

Artifact suppression is therefore a highly sensitive technique and presently only used in situations where a clear and easy cut can be made between the artifact and the useful physiological signal, such as in the above-described case of electrosurgery signal suppression. A breakdown of currently used artifact suppression technologies is contained in the article "Intelligent Detection of Artifact" by I. J. Rampil, published in: Gravenstein et al., "The Automated Anesthesia Record System and Alarm System", Edition Butterworths, 1987.

The present invention relates particularly to artificial artifact detection/suppression in an invasive (e.g., arterial) blood pressure measuring system. Most blood pressure monitors presently available produce a significant amount of false-positive alarms caused by various sources, such as an over- or underdamped tubing system, catheter flushing etc. See the above cited Rampil publication for further reference.

Rampil discusses several known technologies for artifact suppression in an arterial blood pressure monitoring system, namely comparison of the blood pressure with amplitude limits, consideration of the pressure derivative, frequency analysis, pattern searching or an adaptive filter. All of these known techniques are unreliable and/or time-consuming and expensive to implement. For example, the amplitude limit method does not care of disturbers which produce noise of limited amplitude, and may even suppress physiological alarms. Similar considerations apply to the pressure derivative method—most disturbers produce raising and falling edges in physiological regions. The frequency analysis method requires fast Fourier or Walsh transformation which implies a lot of programming effort, and CPU time. This applies also to digital filtering; both methods are further not safe against the suppression of physiological alarms. Similar considerations are true for the pattern search technique which requires a matched filter or like elements, and which has—to applicant's knowledge—not yet been tested in practice. The adaptive filter of ELLIS (see U.S. Pat. No. 4,667,680) was not designed to suppress all kinds of disturbances; in effect, some of the most serious sources of disturbing noise, namely taking of a sample, and catheter flushing (see discussion below), cannot be detected/ suppressed by the ELLIS filter. In fact, applicant uses the ELLIS method in its proprietary monitors, and although it has proven valuable for blood pressure calculations, applicant has still found that additional artifact suppression techniques may be desirable. The present invention was even made in an attempt to overcome the drawbacks of the ELLIS method.

Consequently, there is a continuing need for an improved artifact detection technique in blood pressure measuring systems which avoids the disadvantages encountered with the prior art techniques, either partially or completely.

SUMMARY OF THE INVENTION

It is thus a major object of the present invention to provide a method for detecting/suppressing artificial artifacts in a blood measuring system of the kind described above which operates reliably.

According to the present invention, this object is solved by the following steps:

obtaining a time sequence of samples representative of the actual blood pressure of a being, preferably a human being, calculating a mean value based on preceding values of the blood pressure, comparing at least one of said samples of said time sequence with said mean value, repeating said step of comparing, or said steps of calculating and comparing, for a predetermined number of samples, or for a predetermined amount of time, indicating an artificial artifact if basically all of said comparisons revealed that the samples exceeded said mean value.

The time samples representative of the actual blood pressure of a patient may be digitized samples of a pressure transducer. However, it is understood that preprocessed samples may be used as well. Preprocessing may, e.g., include filtering or averaging. For example, applicant's monitor samples the blood pressure at intervals of 8 milliseconds (which corresponds to 125 Hz). However, it has turned out that a sampling rate of 125 Hz is not required by the present invention. Therefore, 4 (original) samples are averaged to produce a time sequence of (averaged) samples at 32 millisecond intervals. Basically, it is advantageous to select the averaging period as long as possible (i.e., without affecting the inventive method's performance) in order to save CPU time. Therefore, it will be appreciated that the term "actual" does not mean that the sample must occur at the very same point in time as it is processed—in fact, there may be a considerable time delay between the actual occurrence of a blood pressure sample and its occurrence in the time sequence of samples (e.g. caused by CPU overload).

Other preprocessing methods (like gain adjust, 50 Hz notch filtering etc.) may be provided as well.

A mean value is then calculated based on preceding values of the blood pressure. This mean value will also be called "comparison value" hereinafter. It is the purpose of the comparison value to provide a long-term or mid term average of the blood pressure, i.e., it represents the blood pressure history.

In an preferred embodiment of the present invention, a mean blood pressure value is calculated between every heart beat detected (i.e., every pulsation). This is also called "mean beat-to-beat blood pressure". The method described in the above mentioned ELLIS patent (U.S. Pat. No. 4,667,680, which is hereby incorporated by reference) is used to calculate the mean beat-to-beat blood pressure. "Mean" in this context expresses that the mean blood pressure during one pulsation is calculated (as well as systolic and diastolic blood pressures; however, these latter are not used in the preferred embodiment of the present invention).

The above mean beat-to-beat blood pressure is used to calculate the comparison value. Preferably, 16 subsequent mean beat-to-beat blood pressure values are averaged to obtain the comparison value. However, the number of averaged mean beat-to-beat values may also be varied according to the demands of the application.

The just described averaging method relates to a preferred embodiment of the invention. Extensive tests carried out by the inventors have revealed that the method of a "moving average", i.e., an average calculated over a fixed time window, is the best approach to meet the needs of artifact detection, as the resulting comparison value reflects accurately the history of the patient's blood pressure, while it still follows changes of the blood pressure fast enough. Such a moving average may be characterized by the following formula:

$$\overline{m}(t) = \frac{\sum_{i=1}^{n} m_i(\text{pulse})}{n}$$

wherein $\overline{m}(t)$ is the mean or comparison value, and the $m_i(\text{pulse})$ are the mean beat-to-beat blood pressure values. As mentioned above, n is preferably selected as 16.

However, it will be appreciated that other methods of calculating the mean or comparison value may apply as well (although they might be not as effective as the above-described moving average method). For example, a recursive mean value may be calculated, according to the following formula:

$$\overline{m}(t) = a \cdot \overline{m}(t-1) + (1-a) \cdot m_i(\text{pulse}) \text{ with } a < 1$$

However, the mean value (comparison value) may not only be calculated on the basis of the mean beat-to-beat blood pressure. Instead, it is also possible to use the above-mentioned time sequence of samples to calculate the mean value (e.g., by selecting an averaging interval of sufficient length); other parameters relating to blood pressure (e.g., a fraction of the systolic blood pressure) may be used as well. However, the basic difference between the above-mentioned time sequence and the mean value (comparison value) is that the latter is averaged over a longer time period, or with a considerably higher time constant; in other words, the mean value represents a considerably longer time history, or considerably more previous values, of the blood pressure than the time sequence of samples. This means that the mean value (comparison value) is a long-term average, as compared to the time sequence of samples. (Of course, this applies only when the time sequence of samples is averaged at all).

In the next step, at least one of said time sequence samples is compared with the mean value (comparison value). (It will be appreciated that it is likewise possible to compare a value derived from the time sequence sample, e.g. a short-term average, or another derived value, with the comparison value). If this condition is "true", it indicates an overshoot of the time sequence of samples over the long-term or mid-term comparison value, which in turn may be a (first) indication of an artificial artifact.

However, such an overshoot may also occur during normal operation. The present invention therefore provides a time qualifier; i.e., the above condition has to be true for a certain amount of time, basically without interruption. This is called the "confirmation" of the once detected overshoot. The time qualifier can be realized by simply performing the above comparison for a set of subsequent samples. If all of these comparisons reveal that the respective time sequence samples have an amplitude larger than the comparison value, this is regarded as a clear or definite indication of an artifact. (In another embodiment, it may also be sufficient if only a specified majority of comparisons reveals a positive result, i.e., time sequence samples exceeding the comparison value.)

The time period for confirmation, i.e. the period during which the equation $$\overline{s}(t) > \overline{m}(t)$$

($\overline{s}(t)$ representing the time sequence of samples and $\overline{m}(t)$ representing the mean value) has to be true, may be selected according to the specific needs of the application. In the present case, the inventors have found that a time period of 2 seconds reveals excellent results.

The preferred method of checking the validity of this equation during said time period is to repeat the steps of comparing, or the steps of calculating and comparing, for the predefined time period. For example, a sample of the time sequence may be calculated in specific time intervals, and at the same points in time, the mean value (comparison value) is calculated, and the comparison is performed. (The time interval has been selected as 32 milliseconds in a specific embodiment of the present invention. This time spacing has sufficient resolution to detect artificial artifacts reliably, whereas only little CPU time has to be spent. However, it will be understood that this is a non-limiting example).

Alternatively, it is also possible to calculate the mean value only once at the beginning of a time period and to use this value as a reference for the samples of the time sequence during the time window. All of these embodiments are covered by the present invention.

The above disclosed method of selecting a time period criterion (e.g., 2 seconds) is only one possible solution of checking the validity ("confirmation") of a suspected artifact. It is understood that other similar criteria may be used as well, e.g. comparing a predetermined number of samples, and the like.

Advantageously, the artifact indication is used to suppress or disable an alarm, such that the above described problem of false-positive alarms is reduced or eliminated.

The present invention is, to some extent, based on the finding that most artificial artifacts result in a quite rapid increase of the amplitude of the measured blood pressure. However, the rapid increase (i.e., the first derivative of the blood pressure trace over time) as such is not a sufficient criterion, for two reasons:

First, the normal blood pressure sometimes also shows rapid increases. Thus, the derivative of the blood pressure trace (over time) may be high in either case, and an artificial artifact detection method based on the (first) derivative would sometimes also disable "real" alarms (remember that real emergencies must not be suppressed !).

Second, the derivative itself may vary considerably, depending on the reason for the artificial artifact. For example, catheter flushing produces a considerably stronger gradient than taking of a blood sample. Thus, it is difficult to specify a "band" of derivatives which covers all cases of artificial artifacts, but still does not conflict with physiological waveforms.

A simple amplitude limit is also not appropriate, because baseline shifts and other effects may impair artifact detection and even suppress emergency alarms.

The present invention is based on the finding that an "overshoot" in the blood pressure wave may indicate an artificial artifact, but only if two additional conditions apply:

First, the overshoot has to be of considerable time duration. Therefore, the method according to the present invention checks for the time (e.g., 2 seconds) during which the overshoot condition is true.

Second, the determination (or definition) of the "overshoot" itself has to be adapted to the particular physiological wave. This is achieved by adapting the mean value (comparison value) to the history of the blood pressure wave. Thus, the mean value is "self-adapting" to changes in the physiological signal (blood pressure wave), e.g., baseline shifts or low-frequency variations.

Although the inventive method may be used to detect a variety of artificial artifacts, it has proven particularly successful in the detection of artifacts caused by sampling or catheter flushing in an invasive blood pressure measuring system. (In fact, the present invention was made in the course of a study on flush and sample suppression.)

It is a major achievement of the present invention that flushes as well as samples—despite their different patterns in a blood pressure wave!—are detected reliably, without triggering on real (physiological) alarm conditions. That is, clinical reliability is one of the most important advantages of the present invention. It may be even used in a situation, namely flush and sample detection and suppression, in which known artifact detection methods failed or were not used at all, due to their unreliability.

It is another advantage of the present invention that is easy to implement, even in existing blood pressure measuring systems, with only little (programming) effort.

Further, the inventive method requires only little amount of CPU time, such that there are no additional requirements (such as a faster, or an additional processor) concerning the hardware components of the blood pressure measuring system.

The method according to the present invention provides automatic adaptation to varying physiological waves; i.e., it can be used without specific adaptation to the patient (for example, no distinction has to be made between adults and neonates). Still it does not trigger on accidental events with high amplitude, such as muscle artifacts.

It is a further advantage of the present invention that the method is suited for all kinds of invasive blood pressures used in clinical practice, even without specific adaptation. Blood pressures of this kind are, for example, arterial mean blood pressure (ABP), pulmonary arterial blood pressure (PAP) and central venous pressure (CVP).

It is understood that all of the above advantages of the present invention also represent objects solved by it.

It has already been outlined above that the preferred method of calculating the mean value (comparison value) is to use a moving average of the mean beat-to-beat blood pressure. In particular, the moving average quickly and easily adapts to baseline fluctuations or shifts, without affecting other performance characteristics.

In an advantageous embodiment of the present invention, an artificial artifact is—in addition to the above described requirements—only of the predetermined number of samples, or the samples during the predetermined amount of time, exceed, or are equal to, a predetermined threshold. That is, in addition to the criterion $$\bar{s}(t) > m(t),$$

and the related time qualifier, the condition $$\bar{s}(t) \geq s_{min}$$

has to be true.

Purpose of the additional minimum criterion is to reduce the number of false-positive alarms further—a pattern below a certain level, here $S_{min}$, cannot qualify as an artifact. A limit of $s_{min} = 4$ kPa (30 mmHg) has proven very effective in practice. Preferably, the minimum criterion is also subject to the time qualifier—i.e., an artifact is only indicated if this condition is held true for a predetermined time period.

According to another, most advantageous feature of the present invention, an artificial artifact is only indicated if the difference between basically every sample and the sample preceding it in time is greater than, or equal to, a predetermined limit, said samples being samples out of said predetermined number of samples, or being samples occurring during said predetermined amount of time. This condition may be applied in addition to the first, or the second, or both of the above-described conditions. Likewise, it may also be subject to the time qualifier.

In effect, the latter criterion may be expressed by the relation $$\Delta(t) \geq \Delta_{min} \text{ with } \Delta(t) = \bar{s}(t) - \bar{s}(t-1)$$

(or, which is effectively the same if equal time spacing is provided, $$\frac{d\bar{s}(t)}{dt} \geq \left(\frac{d\bar{s}}{dt}\right)_{min}$$

This additional criterion ensures that no strong negative gradient may cause an artifact detection. It is not used to trigger on a strong positive gradient—in fact, the value for $\Delta_{min}$ may even be slightly negative. The preferred value is $\Delta_{min} = -650$ Pa ($-5$ mmHg).

Although all of the above measures and conditions may be used separately, or in any useful combination, it has turned out that a combination of all of them produces excellent results with a detection rate of $>93\%$ of the flushes and samples. That is, the combination of the conditions $$\bar{s}(t) > \bar{m}(t),$$

$$\bar{s}(t) \geq s_{min}$$

and $$\Delta(t) \geq \Delta_{min}$$

was particularly successful and reliable.

The sensitivity of the method according to the present invention may further be advantageously adapted to the history of the blood pressure wave, in order to increase its sensitivity for artifacts. This is achieved by varying the amplitude of said mean value in dependence of preceding detected artifacts. In particular, the amplitude of the mean value may be increased if an artifact has not been detected for a predetermined time period. This decreases the sensitivity of artifact detection. On the other hand, if an artifact has been detected, or ended, only a short time ago, the amplitude of the mean value may be decreased, in order to increase the sensitivity in a situation where a "burst" of artifacts (such as subsequent catheter flushing) occurs.

The detection of the end of an artifact is of similar importance as the detection of its onset, as the reactivation of the alarms—and therefore clinical reliability—depends on it. In respective preferred embodiments of the present invention, the indication of an artifact is removed—and/or the alarms are enabled again—when one of the following conditions occurs:

a) The difference between a sample and the preceding sample falls below a predetermined limit;

b) a (blood) pulsation is detected after the end of an artifact;

c) a sample, or a predetermined number of samples, or the samples in a predetermined time window, fall below a predetermined limit; and/or d) a predetermined time period has expired since its last onset.

All of these conditions may indicate the end of an artifact—condition a) indicates a strong negative gradient, condition b) a physiological event, condition c) the absence of an artifact, and condition d) is a safety measure (the time period is usually selected very long—e.g., 2 minutes—, in order to cover extraordinary circumstances).

In the preferred embodiment, either of the above conditions indicates the end of a detected artifact (i.e., the above conditions are logically OR—connected). However, the present invention also relates to any other logic combination of the above qualifiers (e.g., AND connections and the like).

The invention also relates to a blood pressure measuring system, in particular invasive blood pressure measuring system, comprising:

blood pressure sensing means set up for receiving electronic signals representative of a being's blood pressure from a blood pressure transducer, blood pressure calculating means for calculating the blood pressure, in particular the mean beat-to-beat blood pressure, from said electronic signals received from said blood pressure sensing means, alarm generating means set up to generate an alarm if said calculated blood pressure fulfills at least one predetermined alarm condition, in particular if it falls below or exceeds a predetermined limit, artificial artifact detection means comparing samples representative of said being's actual blood pressure with a mean value based on preceding values of the blood pressure, repeating said comparison for a predetermined number of samples and generating an artificial artifact indicating signal if basically all of said comparisons revealed that the samples exceeded said mean value or values, wherein said artificial artifact indicating signal is fed to said alarm generating means causing the alarm generating means to suppress alarms as long as said artificial artifact indicating signal is in its active state.

It is understood and expressly noted that the present invention relates to all useful combinations of the above disclosed features, whether alone or in any other or arbitrary combination.

BRIEF DESCRIPTION OF THE DRAWINGS

The invention will now be explained, by means of a non-limiting example, with reference to the accompanying drawings, in which:

FIG. 8a shows a blood pressure wave and FIG. 8b depicts the effect of artifact suppression.

DETAILED DESCRIPTION OF THE PREFERRED EMBODIMENTS

Figure 1:
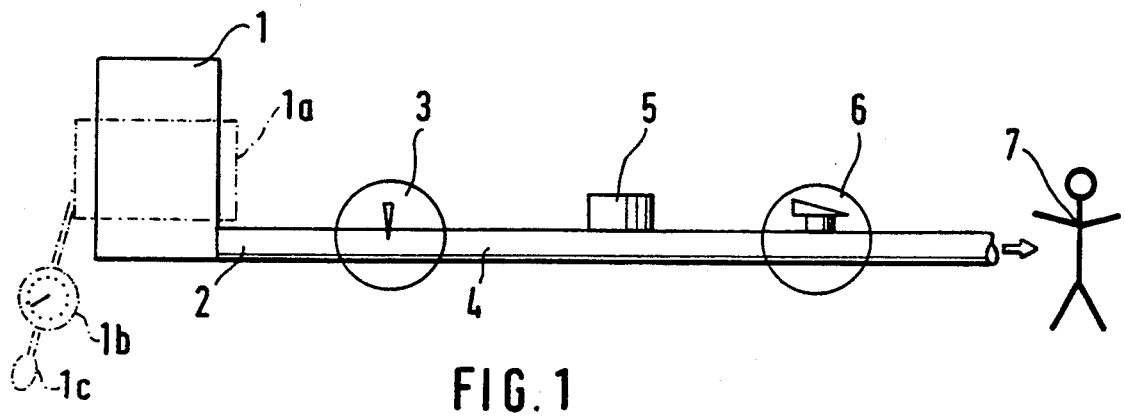
FIGS. 1 to 3 illustrate the effects of taking a sample and catheter flushing in an invasive blood pressure measuring system.

FIG. 1 depicts the basic components of an invasive blood pressure measuring system, e.g. intended for measuring the arterial mean blood pressure (ABP). An infusion solution is stored in container 1 (usually an infusion bottle under the pressure of a pressure bag, as indicated by dotted bag 1a, pressure manometer meter 1b and pressure source 1c in FIG. 1) and connected, via a pressure cuff 2, with a valve 3. Shown in FIG. 1 is the half-opened state of valve 3. The pressure cuff further connects valve 3 with a blood pressure transducer 5 (cf. ref. no. 4) and a three-way cock 6. The latter is in connection with a patient 7, usually via a catheter (not shown).

Figure 2:
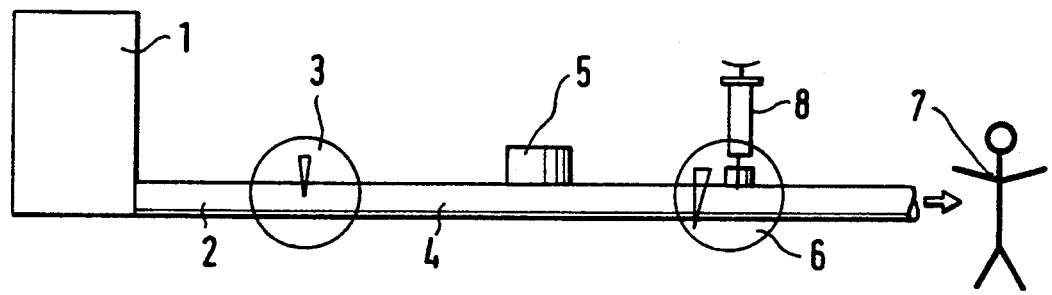

In operation, three-way cock 6 is closed (as shown in FIG. 1), such that blood pressure transducer 5 measures the patient's blood pressure (i.e., the pressure of the infusion solution does not influence the measurement). However, the situation is different in case a blood sample is taken. This is illustrated in FIG. 2.

For the purpose of convenience, the tubing system is used to take the blood sample. Three-way cock 6 is turned such that the connection between the infusion solution and the patient is interrupted. Instead, the cock provides direct access from the "outside" to the patient's blood circulation. In FIG. 2, a syringe 8 is shown in connection with the open port of three-way cock 6, in order to take the blood sample.

Figure 4:
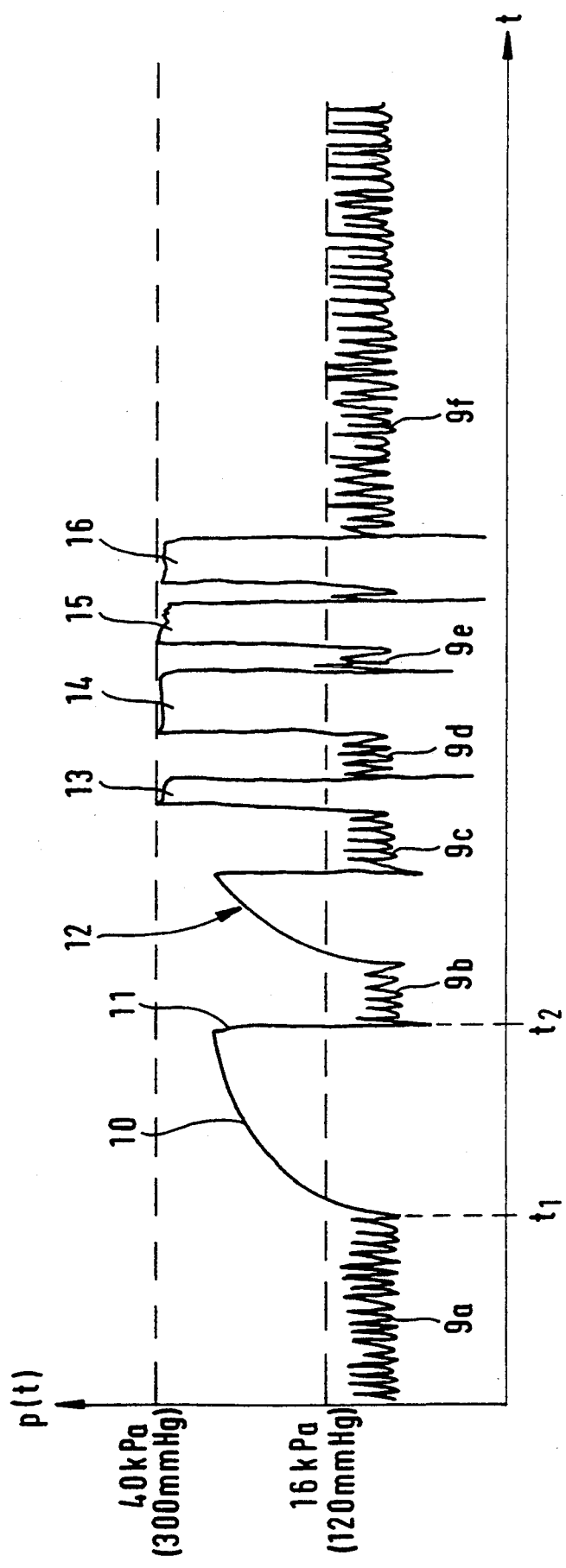
FIG. 4 depicts a blood pressure wave with arbitrary artificial artifacts.

It will be observed that, during the process of blood sampling, blood pressure transducer 5 is no longer connected with the patient, but only with infusion solution container 1. Container 1 is under pressure (for example, typically 40 kPa=300 mmHg), in order to provide continuous cat of FIG. 1. However, one will note that, upon closed three-way cock 6 as shown in FIG. 2, the pressure in container 1 acts on blood pressure transducer 5. However, there is not instantaneous pressure increase at blood pressure transducer 5, due to the half-open state of valve 3. Instead, the blood pressure at transducer 5 is increased at a basically constant, limited rate. This effect is illustrated in FIG. 4 which depicts the arterial blood pressure p(t) of the patient over time t. The regular blood pulsations—corresponding to the mode of operation shown in FIG. 1—are denoted as 9a to 9f. At t=t_1, a blood sample is taken. The resulting increasing blood pressure at transducer 5 is labelled as 10. Upon the end of the blood sampling process, the pressure drops rapidly, as illustrated by reference number 11. FIG. 4 further depicts a second blood sample, see reference number 12.

It will be observed that the blood pressure exceeds a limit of 16 kPa between t=t_1 and t=t_2, i.e., as long as the blood sample is taken. If the limit at p=16 kPa represents an alarm limit, the artifact caused by blood sampling will lead to an (optical or acoustic) alarm. The present invention relates to methods for suppressing such alarms which are not related to physiological events.

Figure 3:
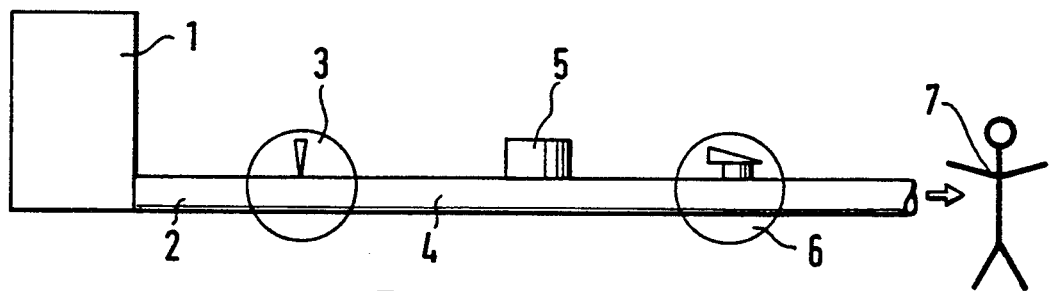

FIG. 3 depicts another mode of operation of the blood pressure measuring system. As the tubing contains human blood after blood sampling, which in turn may lead to clot formation, a strong flush at high pressure (in contrast to the ongoing continuous flush) is necessary. For this purpose, three-way cock 6 is returned to its original position, and valve 3 is completely opened for a time period of several seconds. The high pressure exerted by the pressure bag removes any blood particles.

The effect of catheter flushing is also illustrated in the timing diagram of FIG. 4. Reference numbers 13 to 16 relate to artifacts caused by flushing. It will be noted that the gradients—the positive as well as the negative—are very high. The maximum pressure of flushes 13 to 16 corresponds to the pressure of the pressure bag 1a around container 1.

Artifacts 10 to 16 have a shape which distinguishes them over physiological signals. However, it is not always easy to make a reliable distinction, in particular as alarms caused by suspect or pathologic physiological patterns should never be suppressed, in order to provide patient safety.

Figure 5:
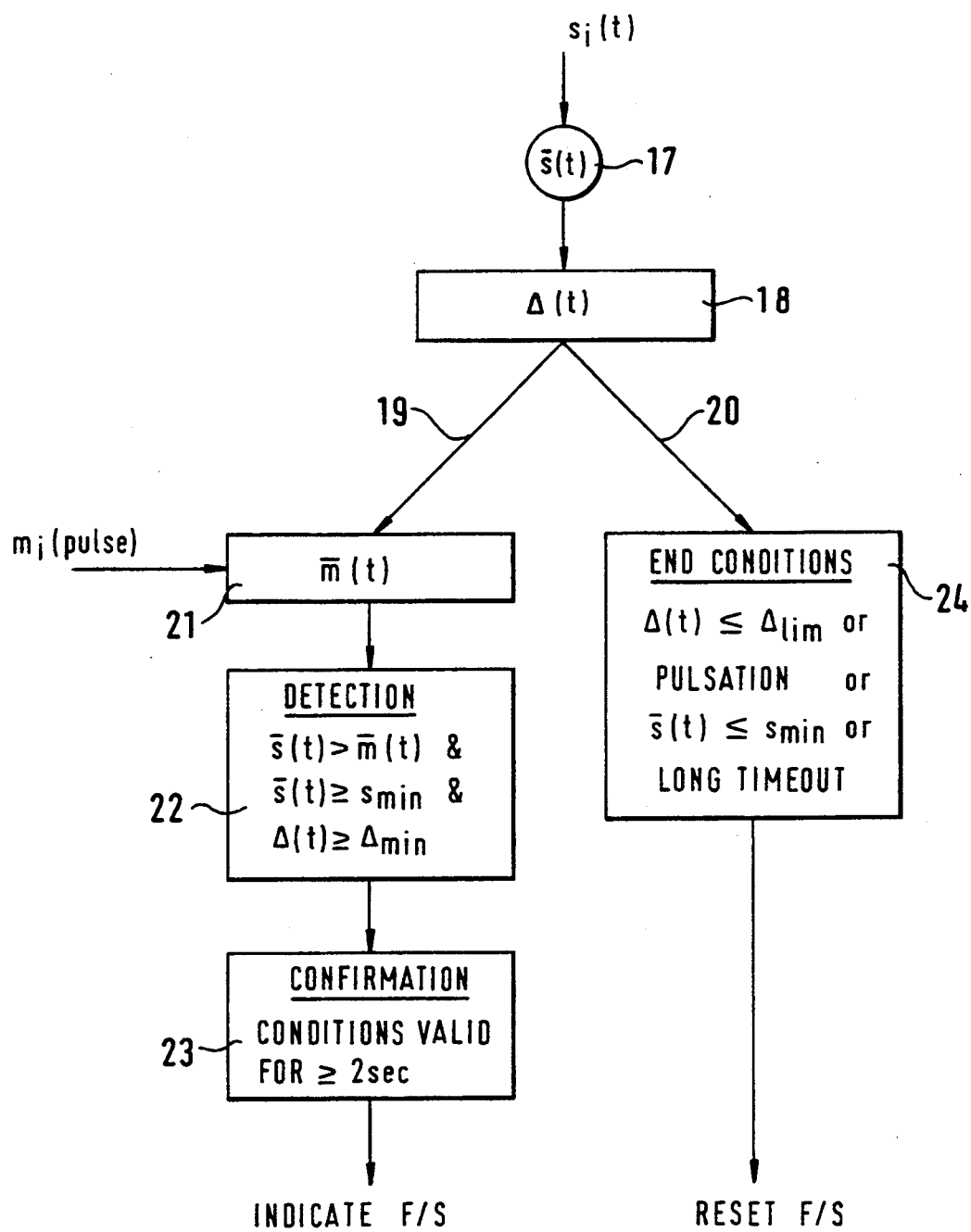
FIG. 5 is a simplified overall block diagram of the present invention.

FIG. 5 depicts a diagram of the basic operation of flush and sample detection/suppression according to the present invention: A monitor samples the blood pressure wave any 8 ms (milliseconds). These samples are labelled as $s_i(t)$ in FIG. 5.

However, it has turned out that the 8 ms interval resolution is not necessary for performing reliable flush and sample detection. Therefore, in order to save CPU (central processing unit) time, an average s(t) is calculated, as indicated by step 17 in FIG. 5. In the specific example described herein, and as will be discussed in more detail below, the average $\bar{s}(t)$ is calculated over four samples.

The next step in the diagram of FIG. 5 (reference number 18) is the calculation of a Δ value labelled as Δ(t). Δ(t) is defined as the difference between one of the averaged samples of step 17 and the preceding sample, i.e., $$\Delta(t) = \bar{s}(t) - \bar{s}(t-1)$$

Operation follows now two different paths, depending on the question whether the beginning or the end of an artifact is searched for. In case the artifact detector is searching for the beginning or onset of an artifact, it proceeds along path 19. Otherwise—i.e., if an artifact has already been detected—, it proceeds along path 20.

Suppose the detector is searching for the beginning of an artifact. In this case, a mean beat-to-beat blood pressure, as e.g. generated by a pressure detector as described in the above-mentioned U.S. Pat. No. US 4,667,680, is used to calculate a mean value or a comparison value. The mean beat-to-beat blood pressure is labelled as $m_i$(pulse) in FIG. 5, and the averaging is indicated by box 21 which provides a moving average (e.g., over 16 mean beat-to-beat blood pressure values) $\overline{m}(t)$.

Operation proceeds now to box 22. The major criteria tested for the detection of artifact onset are:
1. The comparison of the averaged time sequence samples $\bar{s}(t)$ with the mean value $m(t)$, i.e. the test $$\bar{s}(t) > \overline{m}(t)$$

which comparison reveals a positive result in case an "overshoot" of the actual blood pressure samples occurs. $\overline{m}(t)$ herein represents the history of the blood pressure; typically, it is calculated as a moving average.

2. Another condition tested is $$\bar{s}(t) \geq s_{min}$$

wherein the time sequence sample is tested for minimum amplitude. $s_{min}$ may be, for example, 4 kPa (30 mmHg).

3. The third condition ensures that the overall trend is at least slightly positive, wherein small waves should be allowed. This condition is $$\Delta(t) \geq \Delta_{min}$$

Because of the small waves, $\Delta_{min}$ may be slightly negative. Such a value still ensures that there are no strong negative gradients.

It has to be stressed that all of the above conditions have to be fulfilled, in order to detect a flush or a sample; i.e., they are combined by AND logic.

Operation then proceeds to block 23. It relates to the "confirmation" of a once detected suspected artifact. Basically, it checks whether the conditions of block 22 are valid for a predetermined time period (in the present example, 2 seconds).

In case the suspected artifact is not confirmed, operation returns to the top of the diagram in FIG. 5. Otherwise, an artifact is indicated (see label "Indicate F/S" (wherein F/S means "flush/sample") in FIG. 5.

The F/S indication signal is then used to disable an alarm of the blood pressure measuring device. Common blood pressure monitors have an alarm delay anyway, i.e. the alarm is only activated if a certain time period has expired since the detection of the alarm condition. A common value for the alarm delay is 8 seconds. Therefore, an alarm will not occur at all, as the artifact detector disables the alarm already within 2 seconds after the occurrence of an artifact-indicating condition. But even if the alarm handler of the blood pressure monitor would not contain any alarm delay at all, at most a short alarm would be generated, which would, in turn, be disabled prior to any responsive action of medical personnel.

It is of equal importance to detect the end of an artifact such as blood sampling or catheter flushing. This is because the alarm has to be re-enabled as soon as possible. The related path is illustrated by reference number 20 in FIG. 20. The conditions checked for by the artifact detector are listed in box 24. It has to be noted that these end conditions are, contrary to the conditions in box 22, connected by OR logic; that is, the occurrence of one of the conditions in box 24 is already sufficient to indicate the end of an artifact.

Specifically, the end of an artifact is detected if the gradient of the blood pressure wave falls below a predefined limit., as expressed by equation $$\Delta(t) \leq \Delta_{lim}$$

In a preferred embodiment, the limit is set to $\Delta_{lim} = -3.3$ kPa ($-25$ mmHg). This limit may refer to a time interval of 32 msec and thus characterizes a strong negative gradient.

Another condition is the detection of a blood pulsation, because this means that the physiological wave is no longer covered in the noise of an artifact.

Still another condition is that the time sequence sample falls below a certain limit, as expressed by equation $$\bar{s}(t) \leq s_{min}$$

wherein $s_{min}$ is preferably 4 kPa (30 mmHg).

The last condition is a safety measure, in case the artifact detector should—for whatever reason—not return to its initial state. That is, if a certain time period after the onset of the artifact has expired, the artifact detector is reset unconditionally. This criterion is called "Long Timeout". The time period used therefor is preferably 2 minutes.

If one of the above discussed end conditions is detected, the end of the artifact is indicated, see label "Reset F/S" in FIG. 5. The blood pressure measuring device uses this signal to re-enable the alarm.

The flowchart in FIGS. 6a to 6d explains operation of the artifact detector in detail. After entry at the "START" label (reference number 25), the average $\bar{s}(t)$ of several 8 ms-spaced blood pressure values is calculated, see box 26. The number of values $s_i(t)$ is typically m=4, such that $\bar{s}(t)$ represents a 32-ms spacing in time. It will be noted that $\bar{s}(t)$ is a moving average value.

In the next step (box 27), the difference between the averaged blood pressure value and the preceding one is calculated. The difference is denoted as $\Delta(t)$.

The step labeled as 28 tests a flag called F/S_Flag. This is the flag which indicates a detected artifact; i.e., F/S_Flag=TRUE means that an artifact has been detected, and F/S_Flag=FALSE indicates that there is no artifact.

Suppose an artifact has not yet been detected. In this case, the detector searches for the onset of an artifact in that it proceeds to box 29 (the path 30 leading to label "A", which is the path for end detection, will be discussed later).

The operation performed in box 29 is the calculation of a mean value or comparison value $\overline{m}(t)$. In the shown example, the mean value is calculated as a moving average of 16 mean beat-to-beat blood pressure values, i.e., n=16. However, it has to be noted that the mean beat-to-beat blood pressure values $m_i$(pulse) as used herein are an arbitrary selection which has been chosen because a blood pressure calculator producing such values has been available (see the above mentioned U.S. Pat. No. 4,667,680). Other blood pressure values could be used equally well to calculate the moving average $\overline{m}(t)$.

Operation now proceeds to step 31 in which a flag named In__FS__Flag is tested. This is a flag which is set at the end of a detected artifact for a predetermined duration, e.g., 4 seconds. In other words, In__FS__Flag=TRUE means that an artifact has recently occurred.

In case the test in step 31 is negative (In__FS__Flag=FALSE), the mean value $\overline{m}(t)$ is increased by a factor $\alpha$. $\alpha$ is a constant greater than 1; preferably it is 1.5 (150%). By increasing the mean value $\overline{m}(t)$, the sensitivity of the artifact detector is decreased. The corresponding operation is labelled as 32 in FIG. 6a.

In case In__FS__Flag is set, operation proceeds to step 33. In this step, another flag called Long__Timer__Flag is tested. The flag is set whenever a long time out condition occurred, i.e., whenever any extraordinary condition caused a reset of the artifact detector, without any further criteria indicating the end of a flush or sample. As already mentioned, such may occur 2 minutes after the onset of an artifact. (By the way, Long__Timer__Flag is reset as soon as another artifact is detected, as will be discussed below).

In case a long timeout has occurred, i.e., Long__Timer__Flag is set, operation also proceeds to box 32; that is, the sensitivity of the detector is decreased. Otherwise, its sensitivity is increased by the multiplication in box 34. The constant $\beta$ in box 34 is smaller than 1, preferably 0.95 (95%). Both paths are then combined at node 35.

In step 36, $\overline{s}(t)$ is compared with the mean value or comparison value $\overline{m}(t)$. In case $\overline{s}(t)$ is below $\overline{m}(t)$, i.e., no overshoot was observed, operation proceeds to label "C". This is the path to be followed if no artifact has been detected.

Otherwise, the further conditions which have to be fulfilled before a valid artifact is indicated are tested. This is the path leading to label "B" which is continued in FIG. 6b. As box 37 indicates, the next test checks for a minimum value of s(t). $s_{min}$ may, for example, be selected as 4 kPa (30 mmHg). In case this test fails, operation proceeds to node 38 (no artifact); otherwise, the next necessary condition is tested.

This condition is the test for a positive or at least only slightly negative gradient in step 39. $\Delta_{min}$ is preferably −0.66 kPa (−5 mmHg). In case the test in box 39 fails, there is no artifact, and operation proceeds to node 40.

Otherwise, all conditions for valid artifact detection have revealed positive results. As explained above, it has now to be tested whether these conditions remain stable for a certain time period. This is done by incrementing a counter named "Conf__Timer" in step 41 and by comparing it with a maximum value $CT_{MAX}$ in step 42. $CT_{MAX}$ is preferably the equivalent of 2 seconds.

In case Conf__Timer has reached its maximum, a valid artifact is indicated. This is done by setting F/S__Flag, see box 43. Further operations necessary after the detection of an artifact are: Setting In__FS__Flag (box 44); resetting In__FS__Timer, i.e., the timer necessary to control In__FS__Flag, in step 45; and resetting Long__Timer__Flag (box 46).

Next, Conf__Timer is reset, see box 47. Conf__Timer is also reset if no valid artifact has been detected (path 48 and node 49).

In case all artifact conditions (boxes 36, 37 and 39) have revealed positive results, but the 2 second interval is still running (Conf__Timer<$CT_{MAX}$), Conf__Timer is not reset (path 50), and operation proceeds to node 51. Label "D" leads to the exit of the diagram (FIG. 6d), as will be explained later.

The parts of the diagram starting with box 29 and ending with node 51 constitute all relevant steps necessary to detect a valid artifact. As the whole routine is processed every 32 ms, $CT_{MAX}$ may be selected as 64. A valid artifact is then detected after the time period of $64 \times 32$ ms=2048 ms.

Figure 6A:
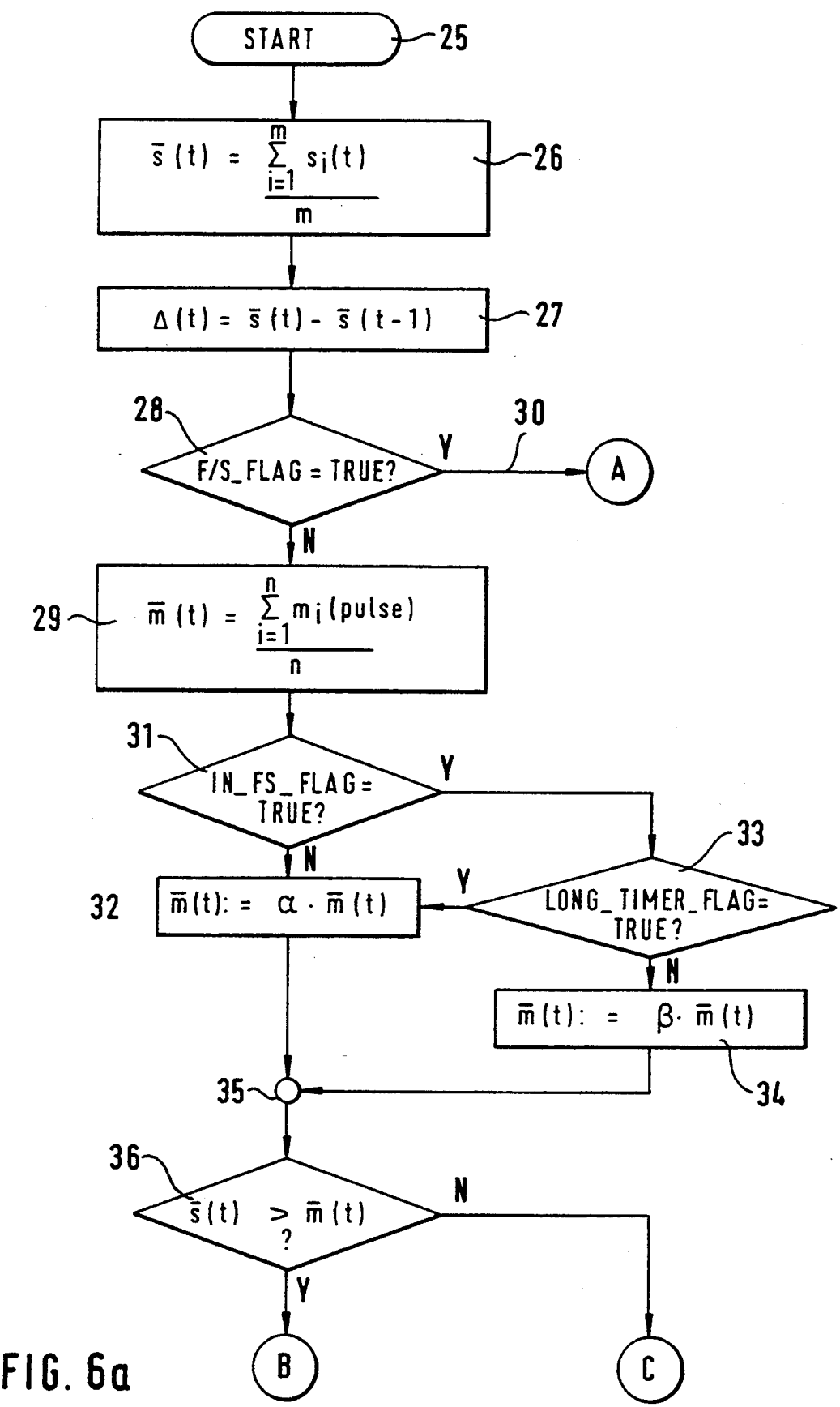
FIGS. 6a to 6d depict a detailed diagram in flowchart form.
Figure 6B:
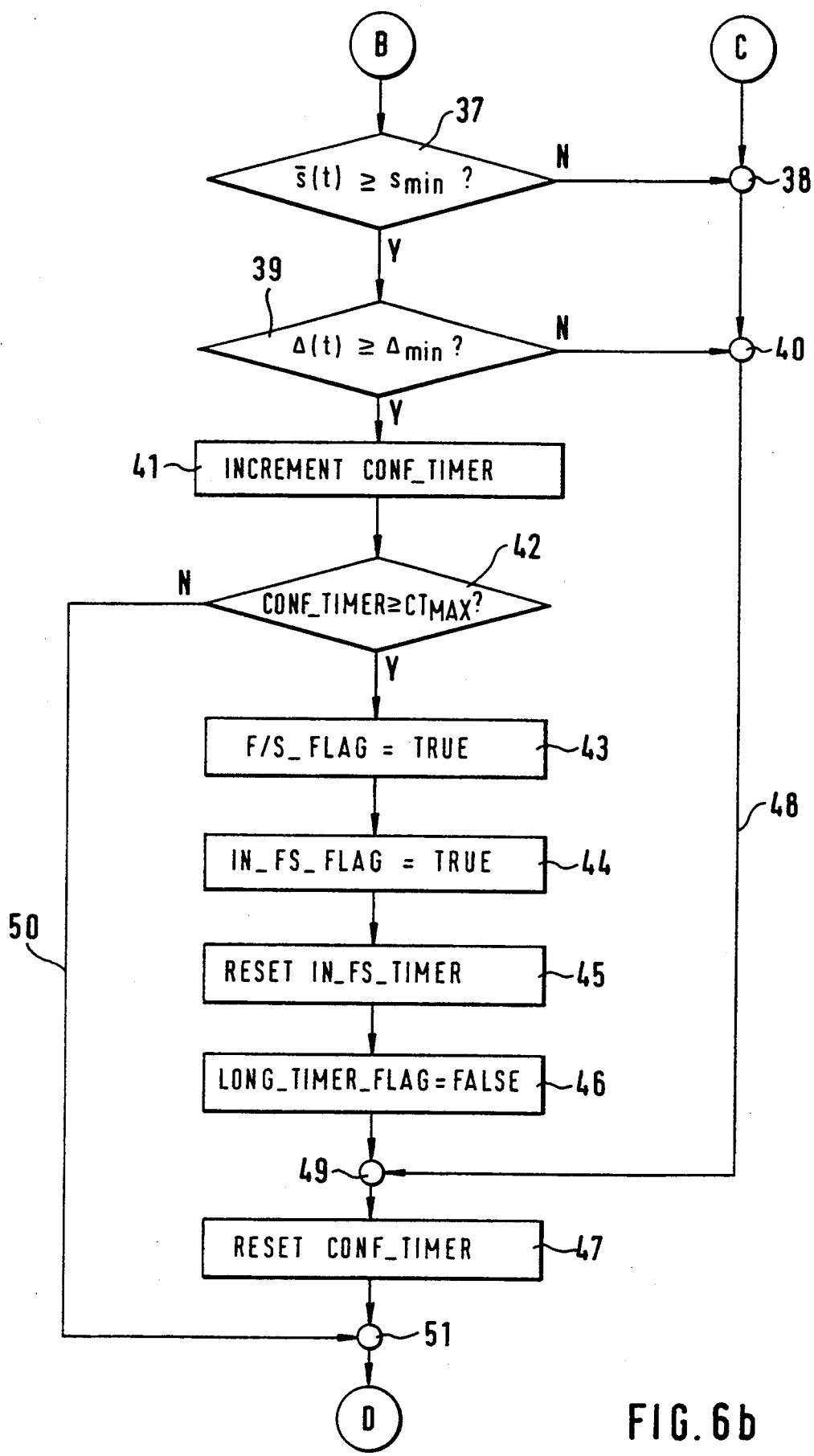
Figure 6C:
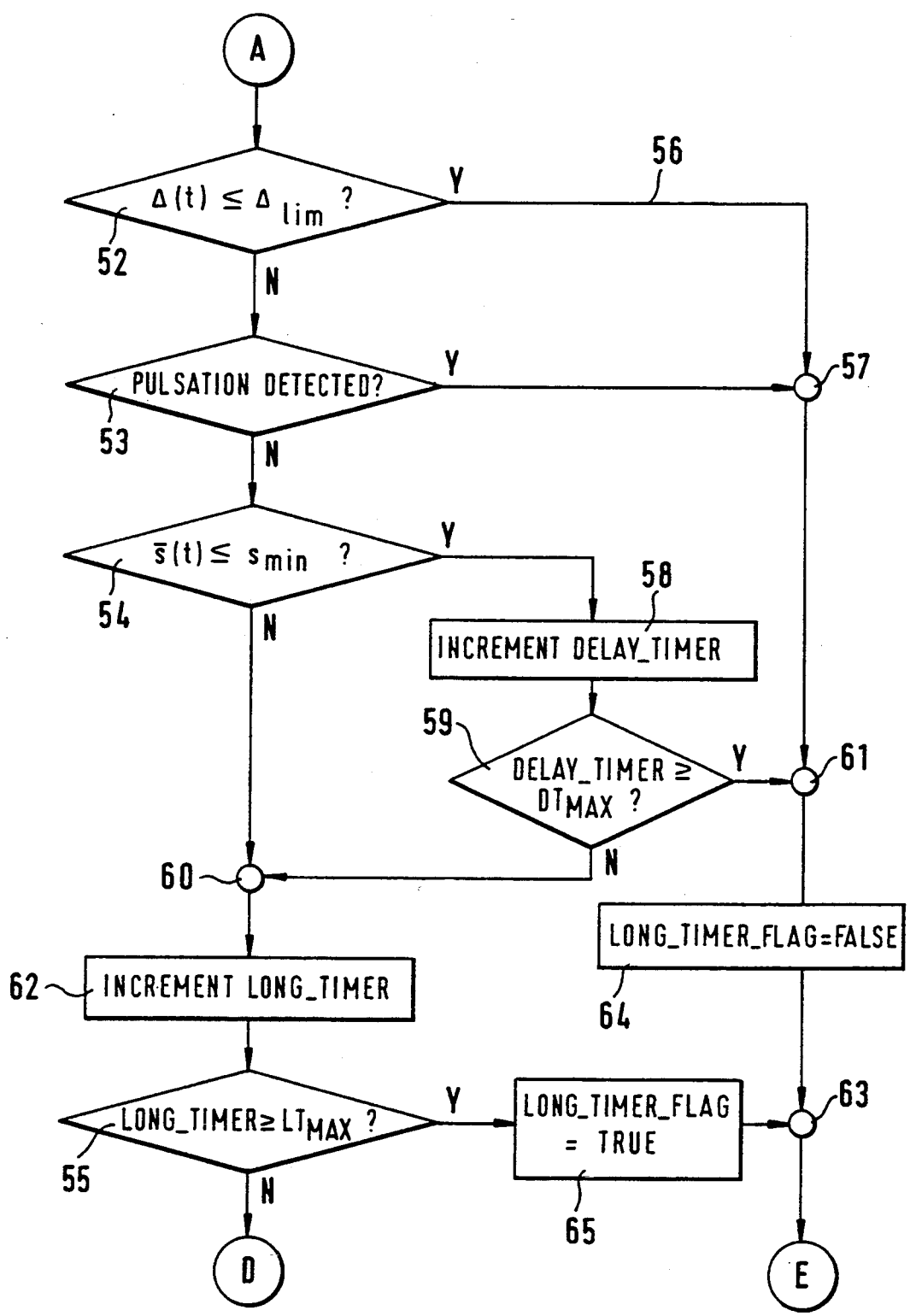
Figure 6D:
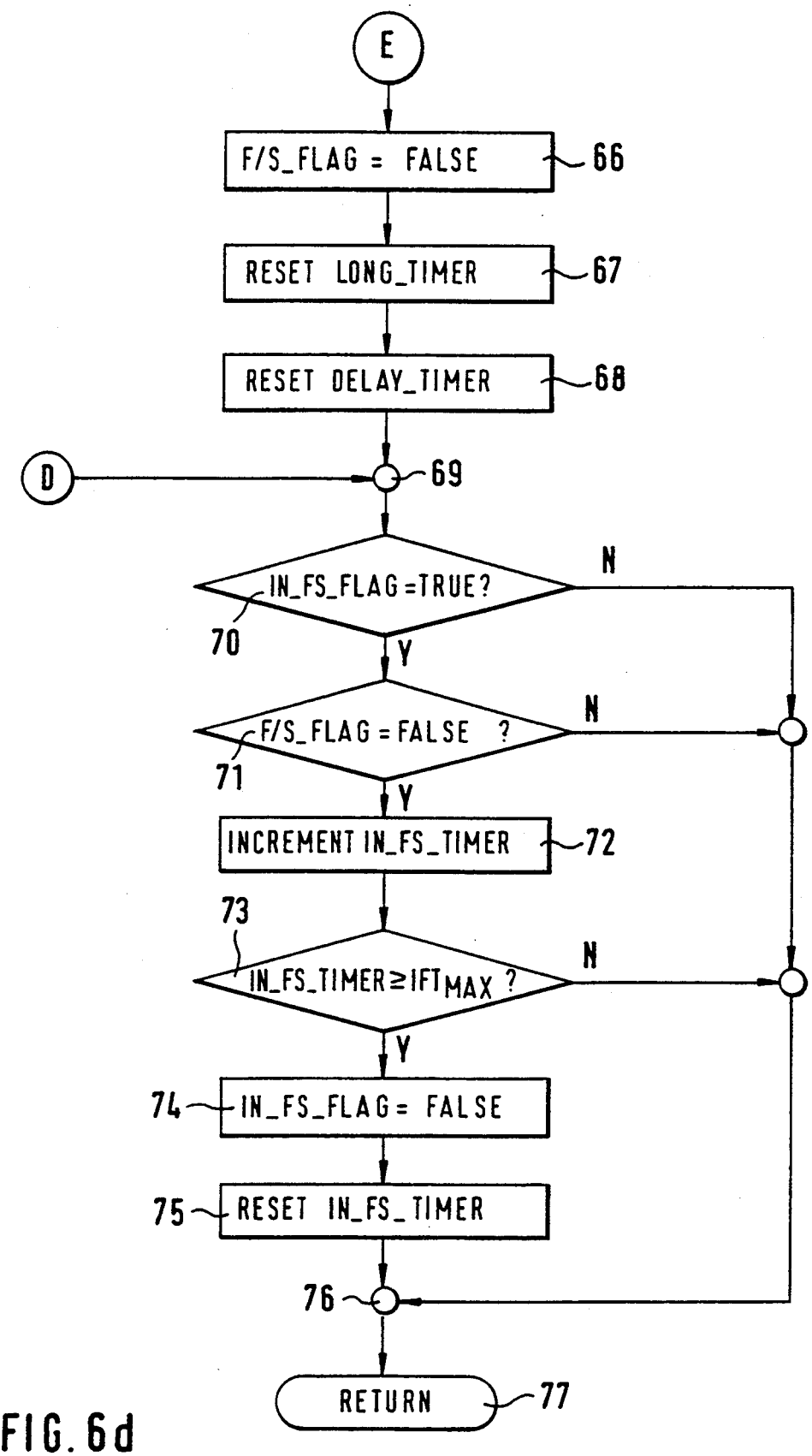

It will be appreciated that various modifications of the flowchart diagram in FIGS. 6a and 6b are possible, without affecting the underlying operating principle. For example, if no indication of blood pulsation is available, the mean value $\overline{m}(t)$ may be calculated in longer time intervals, preferably in intervals of 4 seconds, instead of the 32 ms intervals discussed above. FIG. 6c depicts the necessary steps for determining the end of an artifact condition. It is entered at label "A" if the test in step 28 (FIG. 6a) revealed a positive result.

Various tests are performed in steps 52, 53, 54 and 55 of FIG. 6c. However, it will be noted that already one of these conditions may indicate the end of an artifact, in contrast to the detection of artifact onset, where a multiplicity of conditions has to be fulfilled simultaneously.

In step 52, $\Delta(t)$ is tested against a limit. $\Delta_{lim}$ is preferably $-3.3$ kPa ($-25$ mmHg). A positive result of the test performed in step 52 indicates a large negative gradient of the blood pressure wave which is, in turn, a clear indication of the end of an artifact condition. Operation thus proceeds, via path 56, to node 57.

The next test (step 53) is for a pulsation. Operation proceeds only to the next test—step 54—if no pulsation has been detected. Otherwise, there is a physiological signal again, and the end of the artifact is indicated (node 57). (The reappearance of pulsation may, e.g., be detected by a comparison of $\Delta(t)$ against a fixed limit—e.g., $-800$ Pa=$-6$ mmHg—and/or by an average condition, like $\overline{s}(t) \leq 6.65$ kPa=50 mmHg, or the like. Alternatively, the ranges of $\Delta(t)$ and/or $\overline{s}(t)$ could be stored prior to an artifact, and their later values could be compared against these ranges, in order to determine the reappearance of a pulsation. The latter solution ensures that the blood pressure wave after the artifact equals the wave prior to the artifact).

The test in step 54 is a test for a maximum condition, namely $\overline{s}(t) \leq s_{min}$. $s_{min}$ may be selected as 4 kPa (30 mmHg). A positive result of this test indicates a blood pressure wave of low amplitude.

However, the validity of the latter condition is only accepted if it is stable for a predefined amount of time. This time period is controlled by a timer called "Delay__Timer" which is incremented in step 58. It is then tested against its maximum $DT_{MAX}$ (which may preferably correspond to 1 second) in step 59. In case the timer condition is not yet fulfilled, operation proceeds to node 60. Otherwise, the end of an artifact has been detected, and operation continues at node 61.

Let us focus again on the path after node 60. "Long__Timer" is incremented in step 62, and then the last test for the end of the artifact is performed in step 55 wherein Long__Timer is compared against a limit LT$_{MAX}$ (typically corresponding to 2 minutes). If this condition also does not apply, no "end of artifact" has been detected, and operation proceeds to Label "D" (see FIG. 6d and discussion below).

Now let us return to the cases wherein the end of an artifact has in fact been discovered. This is the path containing node 63 and label "E". Basically, there are two ways to reach node 63: The first is if one of the first three conditions (steps 52, 53 and 54) has applied, in which case Long_Timer_Flag is set to FALSE (box 64). The second is the case wherein a long timeout has been discovered; in the latter case, Long_Timer_Flag is set to TRUE (box 65).

As already mentioned above, the path to Label "E" is the path to be followed if the end of an artifact has been detected. This path is continued in FIG. 6d. In this case, F/S_Flag is reset, i.e., set to FALSE, see box 66 in FIG. 6d. Further, Long_Timer is reset (box 67), and Delay_Timer is reset as well (box 68). Operation now proceeds to node 69.

This is the node where all paths of the operating diagram combine again. It will be noted that node 69 can also be reached via label "D", i.e., the exit of other parts of the operating diagram (see FIGS. 6b and 6c). The rest of the processing diagram is common to all paths. It is simply provided to control the flag which is active for a certain amount of time after the end of an artifact. This flag has been called "In_FS_Flag" above.

First of all, it is tested whether In_FS_Flag is set, i.e. TRUE (step 70). As the time period for In_FS_Flag starts only after the end of an artifact, FS_Flag must be FALSE. This condition is tested in step 71. If it reveals a positive result, a timer relating to In_FS_Flag and called "In_FS_Timer" herein is incremented, see box 72. It is thereafter tested against its maximum IFT$_{MAX}$, step 73. IFT$_{MAX}$ is preferably selected such that In_F-S_Flag is reset 4 seconds after the end of an artifact. As the processing interval of operation is 32 ms, IFT$_{MAX}$ may preferably be set to 128. This reveals a time period of 128×32 ms=4096 ms.

In case In_FS_Timer has reached its maximum—which means that the time period for In_FS_Flag is over—, operation continues with box 74 wherein In_F-S_Flag is set to FALSE. Further, In_FS_Timer is reset (box 75).

All paths—whether they effect an increment of In_FS_Timer, and whether they reset In_FS_Flag, or not—end up at node 76. The flowchart diagram ends at "RETURN" label 77.

Figure 7:
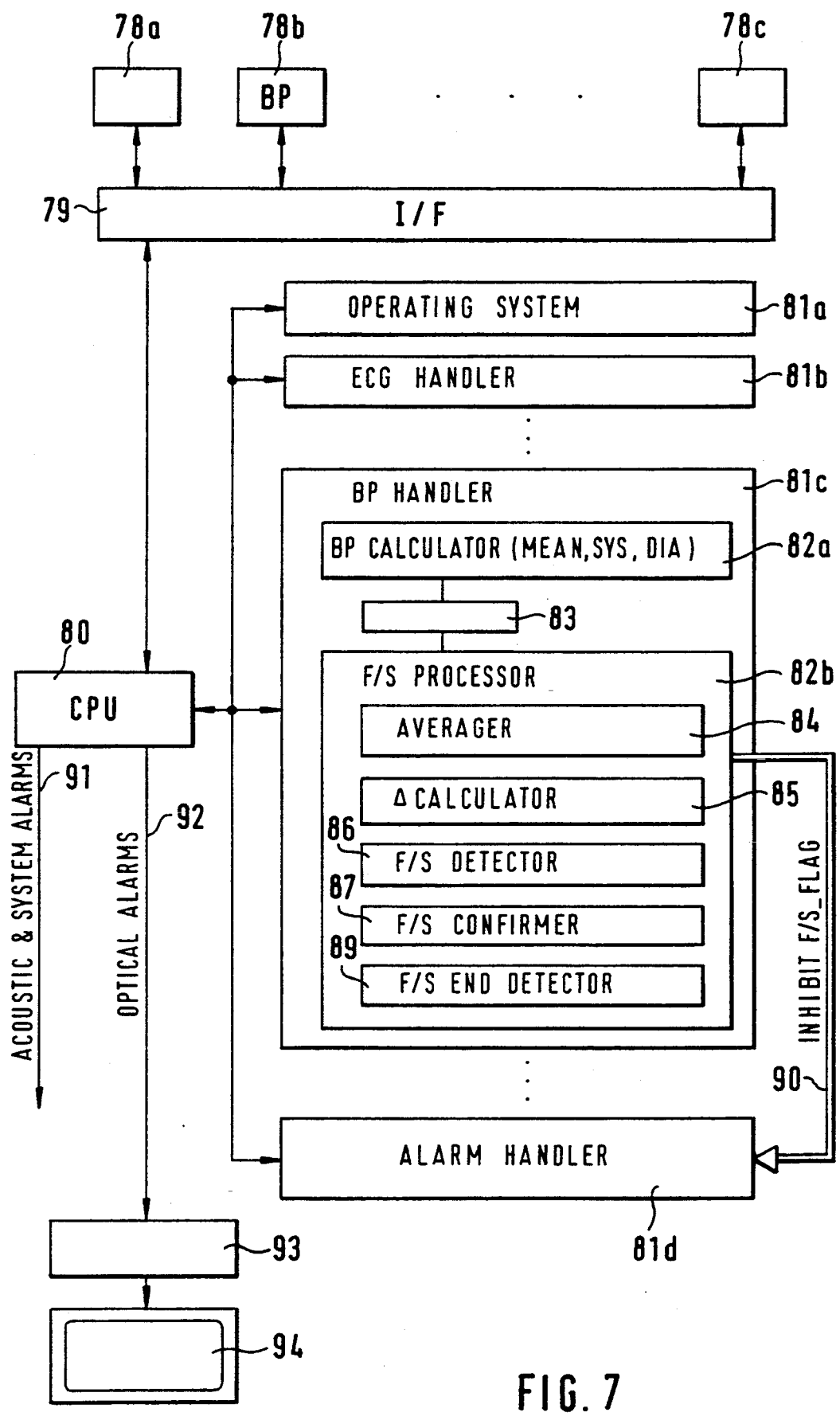
FIG. 7 depicts the components of a medical monitoring system including a blood pressure measuring system and in particular the components related to artifact suppression.

FIG. 7 depicts a medical monitoring system with an invasive blood pressure channel, which in turn contains an artifact detector according to the present invention, in block diagram form. A multiplicity of front end channels or modules 78a to 78c are connected with an interface 79. One of the front end devices is a blood pressure channel or module 78b ("BP" indicates blood pressure).

Front end modules 78a to 78c communicate, via interface 79, with a CPU (Central Processing Unit) 80. CPU 80 operates under control of a multiplicity of modules. First of all, there is the operating system 81a which provides the basic operating functions. Other modules are parameter modules such as an ECG (electrocardiogram) handler 81b, a blood pressure handler 81c and an alarm handler 81d. It will be appreciated that there may be several other modules—e.g., assigned to front end channels such as respiration, temperature, blood gases or other physiological parameters—, which have not specifically been shown in FIG. 7.

Blood pressure handler 81c contains two basic modules. The first is blood pressure calculator 82a which calculates the mean blood pressure, as well as the systolic and diastolic values. Blood pressures of interest may be the arterial mean blood pressure, the pulmonary arterial pressure or the central venous pressure. The operation of blood pressure calculator 82a is disclosed in U.S. Pat. No. 4,667,680. It further provides "wave processing", e.g., scaling and gain adjustment of wave samples.

A second basic component of blood pressure handler 81c is the artifact detector—herein called F/S Processor—82b. It commun calculator 82a via a buffer 83, in particular in order to receive the mean beat-to-beat blood pressure values which have been designated as m$_i$(pulse) above.

F/S Processor 82b contains an Averager 84 which basically performs step 17 in FIG. 5 and step 26 in FIG. 6a. A further component is a Δ Calculator 85, see reference numbers 18 in FIG. 5 and 27 in FIG. 6a.

The artifact or flush and sample detector has been labelled as 86 in FIG. 7. It performs basically the steps of box 22 in FIG. 5, or of steps 36, 37 and 39 in FIGS. 6a and 6b, namely the test for conditions which might indicate an artifact. As already discussed above, these conditions have to be confirmed, i.e., they must be valid for a certain time period. This functionality is provided by F/S Confirmer 87, see reference number 23 in FIG. 5 and references numbers 41 and 42 in FIG. 6b.

Last not least, F/S Processor 82b has also to detect the end of an artifact. This function is provided by F/S End Detector 89, cf. reference number 24 in FIG. 5 and the whole of FIG. 6c.

Whenever F/S Processor 82b detects a valid artifact, the F/S_Flag mentioned above is set. The state of this flag is transmitted to alarm handler 81d and inhibits the same as long as it is set, as illustrated by path 90 in FIG. 7.

CPU 80 also indicates alarms such as acoustic and system alarms (reference number 91), or optical alarms (path 92). The latter are fed, via a video graphics memory 93, to a screen 94, e.g., a CRT (Cathode Ray Tube).

FIG. 8a depicts a physiological blood pressure wave 95 and the mean value or comparison value $\overline{m}(t)$ 96, the latter in dotted lines. FIG. 8b illustrates the status of F/S_Flag, wherein F/S_Flag=1 indicates a detected artifact condition, and F/S_Flag=0 no artifact.

For example, regard the positive gradient of blood pressure wave 95 at reference number 97. This is an artifact which has been caused by taking of a blood sample. Within 2 seconds after its onset, the artifact detector triggers (at t=t$_0$) and disables the alarms. Likewise, subsequent catheter flushing (reference number 98) causes the artifact detector to trigger and to disable the alarms. In both cases discussed above, all of the conditions for an artifact are TRUE; in particular, blood press wave 95 has exceeded the comparison value 96 for more than 2 seconds, which is in fact a basic functionality provided by the present invention.

Similar considerations apply to the blood sampling at reference numbers 99 and 100, and to catheter flushing 101. It will be noted that the small increase at reference number 102 is not detected as an artifact, i.e., it is interpreted as a physiological event.

We claim:

1. A method for detecting artificial artifacts in a blood pressure measuring system comprising the steps of:
   obtaining a time sequence of samples representative of the actual blood pressure of a being,
   calculating a short-term mean value based on preceding values of the blood pressure,
   comparing at least one of said samples of said time sequence with said mean value,
   repeating said step of comparing for a period of time,
   indicating an artificial artifact if substantially all of said comparisons reveal that the samples exceed said mean value, and
   inhibiting said indicating step if pulsations is detected.

2. The method according to claim 1, characterized in that said mean value is a moving average.

3. The method according to claim 1, characterized in that said mean value is calculated from the mean beat-to-beat blood pressure.

4. The method according to claim 1, comprising the additional step of indicating an artificial artifact only if substantially all samples compared during said period of time exceed, or are equal to, a predetermined threshold.

5. The method according to claim 1, comprising the additional step of indicating an artificial artifact only if the difference between substantially every sample and the sample preceding it in time is greater than, or equal to, a predetermined limit, said samples occurring during said period of time.

6. The method according to claim 1, comprising the additional step of varying the amplitude of said mean value in dependence of preceding detected artifacts.

7. The method according to claim 6, wherein the amplitude of said mean value is increased if an artificial artifact has not been detected for a predetermined time period.

8. The method according to claim 1, wherein said indicating step is inhibited if the difference between a sample and preceding sample falls below a predetermined limit.

9. The method according to claim 1, wherein said indicating step is inhibited if a sample falls below a predetermined limit.

10. The method according to claim 1, wherein said indication is removed if a predetermined time period has expired since its last onset.

11. The method according to claim 1, comprising the step of suppressing or disabling an alarm as long as an artificial artifact is indicated.

12. The method according to claim 1, wherein said method is set up for the detection of artifacts caused by sampling in an invasive blood pressure measuring system.

13. The method according to claim 1, wherein said method is set up for the detection of artifacts caused by a flushing in an invasive blood pressure measuring system.

14. The method according to claim 1, wherein the repeating step includes repeating the calculating step.

15. The method according to claim 1, wherein said period of time is defined by a predetermined number of samples.

16. The method according to claim 15, wherein said samples are substantially equally spaced.

17. The method according to claim 1, wherein said period of time is a predetermined amount of time.

18. The method according to claim 1, wherein said indicating step is inhibited if the samples occurring during said period of time fall below a predetermined limit.

19. A blood pressure measuring system, in particular an invasive blood pressure measuring system, comprising:
   blood pressure sensing means for receiving electronic signals representative of a being's blood pressure from a blood pressure transducer;
   blood pressure calculating means for calculating the blood pressure, in particular the mean beat-to-beat blood pressure, from said electronic signals received from said blood pressure sensing means;
   alarm generating means set up to generate an alarm if said calculated blood pressure fulfills at least one predetermined alarm condition, in particular if it falls below or exceeds a predetermined limit; and
   artificial artifact detection means for comparing samples representative of said being's actual blood pressure with a mean value based on preceding values of the blood pressure for repeating said comparison for a predetermined number of samples and for generating an artificial artifact indicating signal if substantially all of said comparisons reveal that the samples exceed said mean value or values unless pulsation is sensed by said blood pressure transducer; wherein said artificial artifact indicating signal is fed to said alarm generating means causing the alarm generating means to suppress alarms as long as said artificial artifact indicating signal is in its active state.

* * * * *

UNITED STATES PATENT AND TRADEMARK OFFICE
CERTIFICATE OF CORRECTION

PATENT NO. : 5,343,868

DATED : September 6, 1994

INVENTOR(S) : Regina Kurscheidt, Martin Felger and Michael P. Beech

It is certified that error appears in the above-identified patent and that said Letters Patent is hereby corrected as shown below:

Column 7, line 12, after "only", insert -- indicated if basically all --.

Column 10, line 2, before "of", change "cat" to --catheter-- and insert -- flushing in the embodiment--.

Column 11, line 23, change "$\bar{s}(t) > \vec{\bar{m}}(t)$" to -- $\bar{s}(t) > \bar{m}(t)$ --.

Column 15, line 65, after "pressure", change "handier" to -- handler --.

Column 16, line 15, after "It", change "commun" to -- communicates --.

Signed and Sealed this

Third Day of January, 1995

*Attest:*

BRUCE LEHMAN

*Attesting Officer*     *Commissioner of Patents and Trademarks*